United States Patent [19]

Mack

[11] 4,194,388
[45] Mar. 25, 1980

[54] CAN TESTING DEVICE

[75] Inventor: Thomas A. Mack, Valparaiso, Ind.

[73] Assignee: Kaiser Aluminum & Chemical Corporation, Oakland, Calif.

[21] Appl. No.: 970,682

[22] Filed: Dec. 18, 1978

[51] Int. Cl.² .............................................. G01M 3/32
[52] U.S. Cl. .......................................... 73/37; 73/49.2; 73/49.8
[58] Field of Search .................. 73/37, 41, 45, 45.1, 73/45.2, 45.3, 45.4, 49.2, 49.3, 49.8, 52

[56] References Cited

U.S. PATENT DOCUMENTS

| | | | |
|---|---|---|---|
| 3,418,845 | 12/1968 | Helms | 73/49.8 X |
| 3,672,208 | 6/1972 | Pearce | 73/49.2 |
| 4,118,972 | 10/1978 | Goeppner et al. | 73/49.2 X |

Primary Examiner—Gerald Goldberg
Assistant Examiner—Joseph W. Roskos
Attorney, Agent, or Firm—Paul E. Calrow; John S. Rhoades

[57] ABSTRACT

The instant invention relates to a device for testing the end buckling strength of a can body wherein a uniquely disposed compressible ring- or doughnut-like member of appropriate elastic material is adapted to be compressed against the inside surface of a metal or container for the purpose of sealing the interior of the metal can from the atmosphere. The sealed interior of the can is then subjected to appropriate fluid or air pressure to determine the buckling characteristics of the can's closed end structure, after which the can body can be released from the testing device in an improved fashion.

16 Claims, 2 Drawing Figures

CAN TESTING DEVICE

BACKGROUND OF THE INVENTION

The instant invention relates to a device for testing the strength of metal cans. More particularly, it is concerned with an improved device for testing the buckling strength of a closed end metal can body. Quality control practices presently used in the manufacture of seamless metal cans, such as those produced by the draw and iron process, or cans wherein the side and one end are integral, require that specimen cans be periodically and randomly removed from the production line prior to filling and placed in an end buckle-testing device for the purpose of determining their respective end buckling strengths.

The buckle strengths required for various commercially acceptable can bodies depend upon the particular structure of the can involved and the product to be packaged in the can. For example, the integral end of a seamless drawn and ironed aluminum can body used to package beer may, according to present packaging standards, have to possess a minimum 88 psi end buckle strength to be acceptable commercially. Prior art machines used for making the above tests were not always easy to operate or maintain and sometimes posed safety hazards to the operator.

For example, some prior art can-testing machines would not readily accommodate cans of varying sizes or slightly uneven open ends and then tightly hold and seal the can interiors from the atmosphere during testing. Others required operators having a certain amount of strength and were susceptible to jamming. Still other types of testing equipment that have been used in the past as buckle testers have permitted the can ends and/or bodies to become so deformed during testing that they would become bound or frozen to the machine, whereby they could be extracted only with extreme difficulty and by means of special tools.

Typical can body wall and/or end testing devices representative of the prior art are illustrated in U.S. Pat. Nos. 715,324; 1,118,478; 2,696,106; 3,336,793; 3,418,845; 3,672,208; 4,027,513 and British Pat. Nos. 1,502,555 and 1,518,363, as well as the testers manufactured and sold by the Newby Precision Machinery Company of Tracy, California, and the Altek Company of Torrington, Connecticut, the latter of which used Model No. 9009 to designate the same. The tester of the first-mentioned company utilized a system of externally disposed complex clamping fingers for pressing the can body wall from the outside into contact with a sealing ring disposed on a can-receiving interior mandrel upon which the can was mounted. The tester of the Altek Company utilized an interior mandrel plug means and complex outer toggle arms for forcing a sealing ring associated with the mandrel plug means into contact with the interior wall of the can body and then maintaining said contact. Both of these latter testers, however, were not always reliable. They were difficult to operate and susceptible to jamming.

The instant development is concerned with providing a can end buckle-testing device of improved characteristics and reliable yet simplified design.

SUMMARY OF THE INVENTION

The instant buckle-testing device which either eliminates or subtantially reduces the problems of prior art testers generally involves an air cylinder mechanism which is used to compress in an improved fashion a doughnut-like ring of appropriate elastic compressible rubber or rubber-like material against the inside of a can body and at a point located intermediate the open and closed ends of the can body. The rubber ring is sufficiently compressed to seal off the interior of the can from the outside atmosphere but without effecting such a binding of can body and tester components that easy removal of the can body after testing is inhibited. The electro-mechanical control system for operating the tester is also simplified and includes components that help to free the can body from the tester after completion of the test cycle.

DETAILED DESCRIPTION

Figure 1:
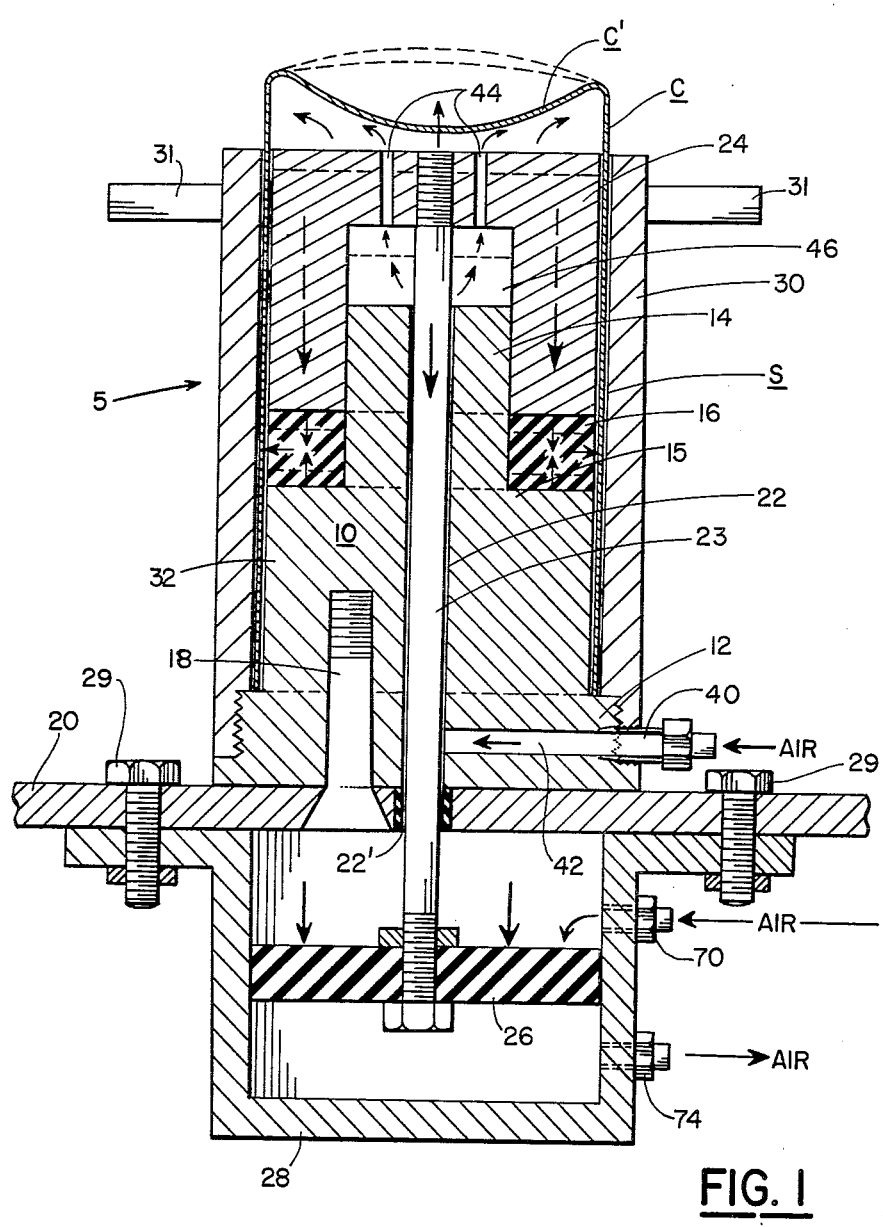
FIG. 1 is an elevational cross-sectional view of the overall can-testing device.

With further reference to the drawings, and particularly FIG. 1, it will be observed that the testing device 5 of the invention is generally comprised of a stepped annular can-receiving mandrel 10. The base 12 of mandrel 10 is advantageously exteriorly threaded and the top and smallest cross-sectional portion 14 of the mandrel is adapted to slidably receive a resilient doughnut-like or ring-like sealing member 16 made from any suitable elastic and compressible rubber or rubber-like material. Sealing member 16 is adapted to be seated on the central step or shoulder 15 of mandrel whereby the ring-like sealing member encompasses a selected part of the mandrel 10 intermediate the ends thereof.

Mandrel 10 is secured by machine screws 18 or the like to a support or service table 20 and includes a central bore 22 for receiving the piston rod 23. Bore 22 registers with opening 22' in service table 20 and opening 22' contains appropriate rod sealing packing. The upper extremity of rod 23 which is accommodated both in mandrel bore 22 and opening 22' in table 20 is secured to an inverted cup-shaped piston 24, while the bottom of rod 23 is affixed to a piston 26 mounted in a flanged cylinder 28 attached to the undersurface of the table 20 by standard bolt assemblies 29. An open ended cylindrical shield or sleeve member 30, the upper portions of which are provided with a greater internal dimension or diameter than the outer peripheries of intermediate mandrel section 32 and the inverted piston 24, is adapted to be threadedly secured to the base 12 of mandrel 10.

If desired, sleeve member 30 can be left threaded onto the mandrel base 12 and be removed only for maintenance purposes, and the insertion of a closed end seamless can body C in the tester 5 can be effected with all parts assembled as shown in FIG. 1 by simply slipping the can body C over the mandrel 10 and fitting the can body wall into the space S between the mandrel 10 and sleeve 30. However, in some instances, the inspector operator may wish to expose the mandrel 10 for the purpose of placing a can body on the same, in which case, he will first remove sleeve 30. Sleeve 30 is equipped with turning bales or handles 31 for use in applying the sleeve to the mandrel. In other words, the can body C will normally fit in the space or gap S located between the sleeve 30, piston 24 and stepped mandrel 10 and not necessarily required removal of sleeve 30 to insert or remove the can body C from the tester 5.

The base of mandrel 10 in the area of section 12 is further provided with an air inlet port 40 which communicates with a horizontal bore 42 that ultimately leads to and communicates with the slightly oversized central bore 22 containing piston rod 23. Cup-shaped piston 24 fitted with air escape openings 44 normally rides over or slides relative to the top portion 14 of mandrel 10 in such a fashion that a small air space or chamber 46 is provided between the piston 24 and the top section 14 of the mandrel. The above-described can-testing device is normally placed in a protective cabinet (not shown) and equipped with appropriate safety glass paneled viewing areas and access doors.

Figure 2:
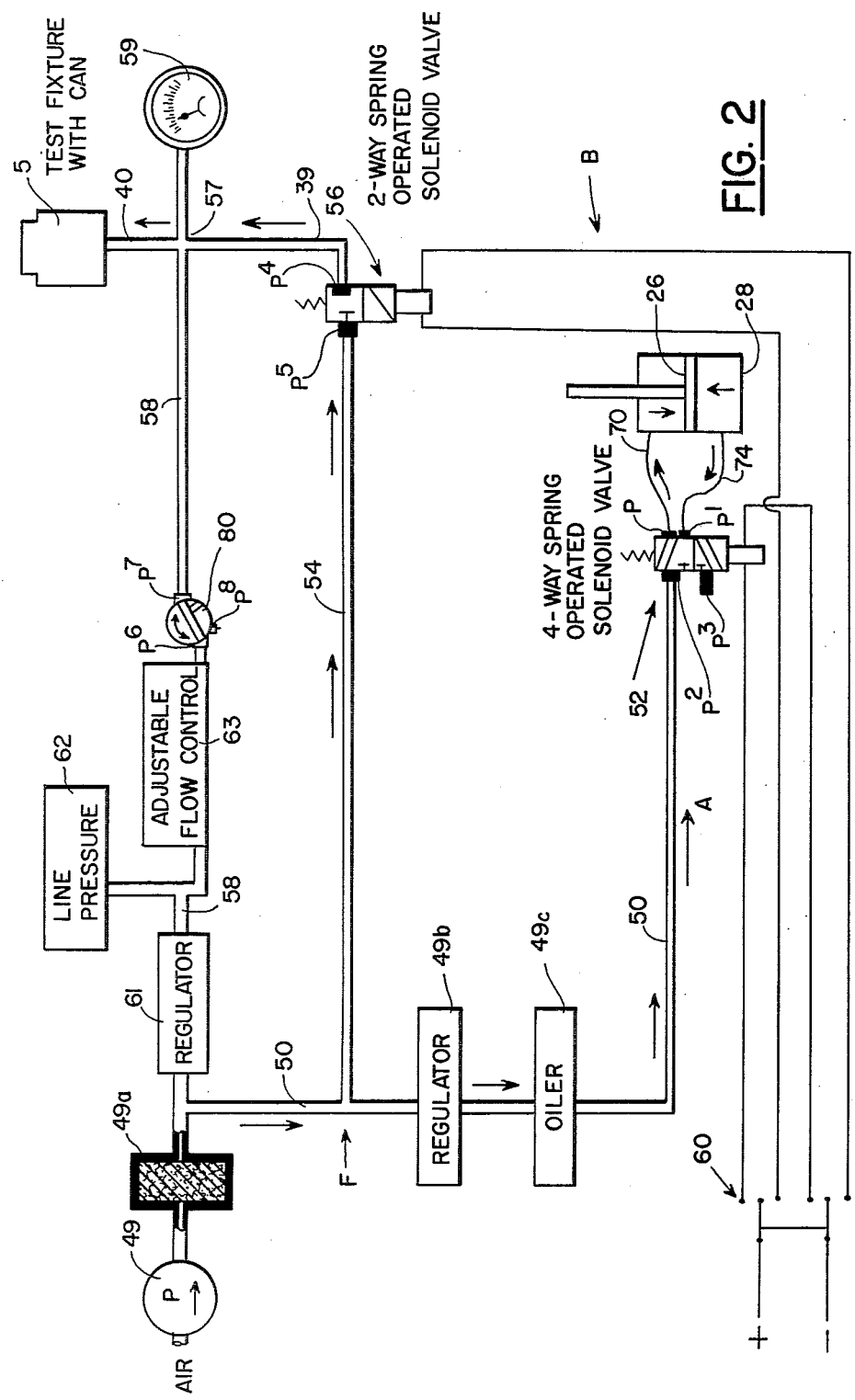
FIG. 2 is a schematic diagram of a suitable electro-mechanical control system that may be employed to operate the can-testing device of FIG. 1.

Reference is now made to FIG. 2 which discloses a suitable electro-mechanical control system for operating tester 5. This system includes the electrical circuit sections A and B, respectively, and a fluid or pneumatic circuit portion F. Pneumatic circuit portion F is provided with main piping line 50 that includes a standard pump 49, an air filter 49a, an air regulator 49b and an air line oiler 49c. Pump 49 is equipped with its own pressure-operated control switch which can be regulated to automatically shut off the pump in a manner well known in the art when the line pressure in the pneumatic circuit exceeds a selected amount, e.g., 115 psi. Line 50 leads to a four-way solenoid-operated valve 52 provided with ports P, $P^1$, $P^2$ and $P^3$. Port $P^2$ connects line 50 to the valve, while port $P^3$ leads to the atmosphere. Ports P and $P^1$ lead to opposite sides of piston 26 located in cylinder 28.

A branch piping line 54 that communicates with main line 50 in pneumatic circuit F is also connected to a solenoid-operated, two-way valve 56 having a port $P^4$ connected by way of line 39 to the air inlet 40 in mandrel 10 and branch line port $P^5$. Pneumatic circuit F further includes a second branch line 58. In addition to being connected to main pipe line 50, line 58 is connected at piping junction 57 to the line 39 between valve 56 and air line inlet 40 of testing device 5 and a pressure gauge 59 for reading the end buckling pressure. A hand-operated standard three-way toggle valve 80 containing ports $P^6$, $P^7$ and $P^8$ is also located in the branch line 58, together with a conventional air line regulator 61, air line pressure gauge 62, and adjustable flow control device 63. Port $P^8$ of valve 80 leads to the atmosphere while ports $P^6$ and $P^7$, when connected, permit air under pressure to pass into the air inlet 40 of mandrel 10.

The electrical control circuit section A for valve 52 is connected to a power supply by means of one part of a double pole switching mechanism 60 that can be hand operated, while the other electrical circuit portion B for solenoid-operated valve 56 is connected to the power source by the other part of the same switch 60. In other words, movement of double pole switch 60 in the proper direction operates to connect the power source to one or the other of the valve solenoids controlling valve 52 or valve 56, while simultaneously deactivating the other solenoid valve in the desired manner.

The operation of the testing device 5 is generally as follows. A can body C is placed over mandrel 10 and slipped down into the space S between the stepped mandrel 10 and the outer sleeve 30 until the open end of the can rests on mandrel base 12. The double pole switch 60 is then operated so as to close the contacts for circuit section A, while deactivating circuit section B by opening the contacts for circuit section B. After manipulation of switch 60 as noted, valve 80 is also manipulated by the operator so as to connect tester 5 with line 58 by connecting ports $P^6$ and $P^7$ to various parts of line 58. With valve 52 activated and valve 56 deactivated, the spring biased spool for the latter valve will bring about a disconnection of ports $P^5$ and $P^4$ of valve 56, whereby the air in line 50 will pass through the ports $P^2$ and P of valve 52 to the top part of cylinder 28 through air line 70. This results in piston 26 being forced down in the direction of the arrows in FIGS. 1 and 2, while air passes out of cylinder 28 through line 74 and then through ports $P^1$ and $P^3$ to the atmosphere. As the piston 26 moves down, it forces the inverted cup-shaped piston 24 against the sealing ring member 16, thereby compressing the rubber doughnut sealing member and forcing it outwardly against the inside surface of the can body wall so as to seal the interior of the can body C from the atmosphere and the can body wall against the outer sleeve 30 which acts to prevent a collapse or deformation of the can body side wall.

In the meantime, the air in mandrel compartment 46, some of which was forced into the compartment at the time the can was placed over the top of the cup-shaped member 24, is evacuated into the upper portion of the can body and against the concave can end C' through the openings 44 in the piston 24 due to the air from branch line 58 which passes through the connected ports $P^6$ and $P^7$ of three-way valve 60. Thus, as air pressure continues to maintain compression of the sealing doughnut member 16 and sealing contact between the can body side wall and member 16, the interior of the inverted can body C above sealing member 16 will then continue to fill with the air passing through air inlet 40 from line 58 until the can end buckles at a pressure that is readily visible on gauge 59 and the air supply cut off by selected operation of valve 80.

As soon as the can end buckles and the testing completed the operator manipulates toggle valve 80 to exhaust air from the can interior by connecting ports $P^7$ and $P^8$ of valve 80 while blocking off port $P^6$, and while also reversing the double pole switch 60. Reversal of switch 60 activates the solenoid for valve 56, thereby connecting ports $P^4$ and $P^5$ thereof, while deactivating the solenoid for valve 52. Deactivation of the solenoid for valve 52 results in the spring biased valve spool of valve 52 moving to connect port $P^2$ with port $P^1$ and port P with port $P^3$, thereby allowing air to enter the bottom of cylinder 28 through line 74 as air at the same time is evacuated from the top of the cylinder through line 70 and ports P and $P^3$. Air now enters the bottom of the cylinder 28 by way of ports $P^2$ and $P^1$ of valve 52 and as piston 26 moves upwardly, it brings about a decompression of the rubber ring 16 and a relaxing of the sealing pressure on the can body.

Simultaneously with the above sequence of events, a brief activation of the solenoid for valve 56 upon a momentary reversal of pole switch 60 as noted will cause connection of ports $P^4$ and $P^5$ and a momentary short burst of air to go directly into the interior of the can body C still on the mandrel of tester 5 but now unclamped so as to help dislodge or free the can from the testing fixture mandrel 10. The switch 60 is then returned to its central or neutral position shutting off power to both solenoid valves 52 and 56 so that the tested can body can be removed and the tester 5 readied for the next can body to be tested.

Although this invention has been described with particular reference to testing the buckling strength of a can end which is formed integrally with the can body, it is equally applicable to testing a can end which has been seamed onto a can body by a standard double seaming operation. In this case, the integral end portion of a drawn and ironed can body which is not to be subjected to the end buckle test is simply cut off to provide an open end which then fits over the mandrel. Also, if the can end being tested is an end for a three-piece can, then one end of the can is simply left off so that the can can be inserted over the mandrel at the open end thereof. Thus, it is to be understood that the term "open ended can body", as used in the claims, is intended to cover a can body wherein the closed end has either been integrally formed with the can body or seamed thereto in the conventional fashion.

An advantageous embodiment of the invention has been shown and described. It is obvious that various changes and modifications may be made therein without departing from the spirit and scope thereof as defined in the appended claims.

What is claimed is:

1. A can end buckle-testing device of the type described comprising the combination of a mandrel means for receiving an open ended can body, a ring-like sealing member of elastic compressible material arranged on said mandrel means so as to encompass a selected portion of the outer part of the mandrel means, a selectively controlled piston means slidably disposed relative to the mandrel means for compressing the sealing member and for forcing the sealing member into contact with the inside of the wall of a can body disposed on the mandrel means, means including piping and valve means for selectively introducing fluid under pressure into and through the mandrel means and into the interior of the sealed can body disposed on said mandrel means and intermediate the sealing member and the end of said can body during compression of the sealing member, and fluid source means connectable simultaneously both to said piston means and said valve means so as to effect introduction of pressure testing fluid into the interior of the can body and against the end thereof simultaneously with the maintenance of the compression of the sealing member.

2. The testing device of claim 1 wherein said mandrel means is provided with a stepped portion and the sealing member is mounted on said stepped portion.

3. The testing device of claim 1 wherein said mandrel means includes a bore means and said bore means includes a section for both receiving a piston rod for said piston means and for passing fluid under pressure into the interior of the can body.

4. The testing device of claim 1 including an open ended sleeve member part of which is attachable to said mandrel means and another part of which is adapted to be located in slightly spaced relationship to said mandrel means so as to provide a space for receiving the side wall of the can body mounted on the mandrel means.

5. The testing device of claim 1 wherein said mandrel means is a rigid and fixed mandrel means that is provided with a stepped portion for receiving the sealing member.

6. The testing device of claim 1 including additional valve means for independently introducing fluid under pressure into and through said mandrel means and against the end of the can body at the end of the can body testing cycle and after pressure on said sealing member is relaxed so as to free the can body from the mandrel.

7. The testing device of claim 6 including a further valve means for operating said piston means and wherein said second- and third-mentioned valve means are solenoid operated and controlled by a double pole switching device.

8. A can end buckle-testing device of the type described comprising the combination of a mandrel means for receiving an open ended can body, said mandrel means being provided with bore means, a ring-like sealing member of elastic compressible material arranged on said mandrel means so as to encompass a selected portion of the outer periphery of the mandrel means, a selectively controlled piston means slidably disposed relative to the mandrel means for compressing the sealing member and for forcing the sealing member into contact with the inside surface of the side wall of a can body disposed on the mandrel means, means including piping and valve means for selectively introducing fluid under pressure into and through the bore means of the mandrel means and into the interior of the sealed can body and intermediate the sealing member and the end of said can body during compression of the sealing member, and a common fluid source means connectable simultaneously both to said piston means and said valve means so as to effect introduction of testing fluid under pressure into the interior of the can body and against the end thereof simultaneously with the maintenance of the compression of the sealing member.

9. The testing device of claim 1 wherein said mandrel means is provided with a stepped portion and the sealing member is mounted on said stepped portion.

10. The testing device of claim 1 wherein said bore means includes a section for receiving the piston rod for said piston means and for passing fluid under pressure into the interior of the can body disposed on said mandrel means.

11. The testing device of claim 8 including an open ended sleeve member, one part of which is attachable to said mandrel means and another part of which is adapted to be located in slightly spaced relationship to said mandrel means so as to provide a space for receiving the side wall of the can body mounted on the mandrel means.

12. A can end buckle-testing device of the type described comprising the combination of a mandrel means for receiving an open ended can body, said mandrel means being provided with bore means, a ring-like sealing member of elastic compressible material arranged on said mandrel means so as to encompass a selected portion of the outer part of the mandrel means, a selectively controlled piston means slidably disposed relative to the mandrel means for compressing the sealing member and for forcing the sealing member into contact with the inside of the wall of a can body disposed on the mandrel means, valve means for controlling said sealing member compressing piston means, piping and valve means for selectively introducing fluid under pressure into and through the bore means of the mandrel means and into the interior of the sealed can body and intermediate the sealing member and the end of said can body during compression of the sealing member, a common fluid source means connectable simultaneously both to the valve means for said piston means and said piping and valve means so as to effect introduction of testing fluid under pressure into the interior of the can body and against the end thereof simultaneously with the maintenance of the compression of the sealing member and a further piping and valve means for momentarily and selectively injecting a small amount of fluid under pressure into and through the bore means of the mandrel means at the end of the testing cycle and upon relaxation of pressure on the sealing member for the purpose of freeing the tested can body from the mandrel means.

13. The testing device of claim 12 wherein said first- and last-mentioned valve means comprise solenoid-operated valves controlled by a common switching means.

14. The testing device of claim 12 including means for operating said first- and second-mentioned valve means independently of each other.

15. The testing device of claim 14 wherein said first- and last-mentioned valve means comprise solenoid-operated valves controlled by a common switching means.

16. The testing device of claim 12 including an open ended sleeve member, one part of which is attachable to said mandrel means and another part of which is adapted to be located in slightly spaced relationship to said mandrel means so as to provide a space for receiving the side wall of the can body mounted on the mandrel means.

* * * * *